(12) United States Patent
Wait

(10) Patent No.: US 11,428,680 B2
(45) Date of Patent: Aug. 30, 2022

(54) TRAIN EMISSION COMPLIANCE SYSTEM

(71) Applicant: NEW YORK AIR BRAKE, LLC, Watertown, NY (US)

(72) Inventor: Keith Wesley Wait, Flower Mound, TX (US)

(73) Assignee: NEW YORK AIR BRAKE, LLC, Watertown, NY (US)

( * ) Notice: Subject to any disclaimer, the term of this patent is extended or adjusted under 35 U.S.C. 154(b) by 78 days.

(21) Appl. No.: 15/407,675

(22) Filed: Jan. 17, 2017

(65) Prior Publication Data

US 2018/0202985 A1 Jul. 19, 2018

(51) Int. Cl.
| | |
|---|---|
| *G01N 33/00* | (2006.01) |
| *B61K 9/00* | (2006.01) |
| *B61L 25/02* | (2006.01) |
| *B61L 3/00* | (2006.01) |
| *B61L 15/00* | (2006.01) |

(52) U.S. Cl.
CPC ............. *G01N 33/004* (2013.01); *B61K 9/00* (2013.01); *B61L 3/002* (2013.01); *B61L 15/0081* (2013.01); *B61L 25/025* (2013.01); *B61L 2205/04* (2013.01)

(58) Field of Classification Search
CPC ........ G01N 33/004; B61K 9/00; B61L 25/025
See application file for complete search history.

(56) References Cited

U.S. PATENT DOCUMENTS

| | | | |
|---|---|---|---|
| 9,744,980 B2 | 8/2017 | Henry et al. | |
| 2005/0251299 A1* | 11/2005 | Donnelly | B60L 7/08 701/19 |
| 2006/0129289 A1* | 6/2006 | Kumar | B60L 11/123 105/26.05 |
| 2006/0266256 A1* | 11/2006 | Donnelly | B60L 7/06 105/61 |
| 2007/0219683 A1* | 9/2007 | Daum | B61L 3/006 701/19 |
| 2007/0233364 A1* | 10/2007 | Kumar | B61L 3/006 701/123 |
| 2008/0033605 A1* | 2/2008 | Daum | B61L 3/006 701/19 |
| 2008/0246338 A1* | 10/2008 | Donnelly | B61C 7/04 307/54 |
| 2009/0132113 A1* | 5/2009 | Kumar | B61L 3/006 701/33.4 |

(Continued)

FOREIGN PATENT DOCUMENTS

WO  2006/012484  2/2006

OTHER PUBLICATIONS

International Search Report Form PCT/ISA/220, International Application No. PCT/US2017/013737, pp. 1-11, dated Oct. 30, 2017.

*Primary Examiner* — Raymond L Nimox
(74) *Attorney, Agent, or Firm* — Bond Schoeneck and King PLLC; David Nocilly

(57) ABSTRACT

A system that can automatically measure, track, and/or report train emissions for complying with geographic environmental restrictions. An emissions module determines the amount of emissions emitted by a train over time. A location module tracks the location of the locomotive of the train relative geographic locations having emission regulations. A compliance module records the amount of emissions emitted by the train in the geographic location.

7 Claims, 2 Drawing Sheets

(56) References Cited

U.S. PATENT DOCUMENTS

2012/0022728 A1* 1/2012 Hall ................ B60L 11/123
                                                                701/19
2014/0207316 A1   7/2014 Kolambekar

* cited by examiner

TRAIN EMISSION COMPLIANCE SYSTEM

BACKGROUND OF THE INVENTION

1. Field of the Invention

The present invention relates to train emission monitoring and, more specifically, to a system that can compute train emissions and ensure compliance with geographic emission policies.

2. Description of the Related Art

Environmental regulations are increasing being placed on railroads by governmental authorities. As a result, railroads have to monitor trains for compliance with the regulations, such as the amount of engine emissions, and report on train operations to the appropriate authorities. For example, restrictions on engine emissions are already in place in some jurisdictions and require that railroads track and report the amount of emissions that are made by a train while it is in a particular zone. Accordingly, there is a need for a system that can more easily measure and track train operations for the purposes of complying with localized environmental regulations.

BRIEF SUMMARY OF THE INVENTION

The present invention is a system that can automatically measure, track, and/or report train emissions for the purposes of complying with geographic environmental restrictions. The system has an emissions module that is programmed to determine the amount of emissions emitted by a train over time. The emissions module is interconnected to at least one sensor that directly measures the amount of emissions emitted by the train. Alternatively, or in addition thereto, the emissions module can receive data representing the current operating conditions of the train and then calculate the amount of emissions based on the data. The emissions module can also receive data representing ambient weather conditions and the use the data representing ambient weather conditions along with the data representing the current operating conditions of the train to calculate the amount of emissions. A location module is programmed to track the location of the train relative to at least one geographic location having emission regulations, such as by using a global positioning system and a track database having the location of emission zones. Finally, a compliance module is programmed to record the amount of emissions emitted by the train in the at least one geographic location. The compliance module may be programmed to compile a total amount of emissions of the train by tracking the amount of emissions emitted by a train over time for the entire time the train is in the at least one geographic location having emission regulations. The compliance module may also be programmed to store the total amount of emissions of the train, to generate a report of the compiled total emissions for each zone, and/or to transmit the report to a remote host.

The present invention also comprises a method of tracking train emissions that begins with determining the amount of emissions emitted by a train over time. This determination may be made using at least one sensor that directly measures the amount of emissions emitted by the train or by calculating the amount of emissions based on operating data of the train. Next, the location of the train is tracked relative to at least one geographic location having emission regulations. Finally, the amount of emissions emitted by the train in the at least one geographic location is recorded by compiling the amount of emissions emitted by a train over time for the entire time the train is in the at least one geographic location having emission regulations. A report of the compiled total emissions for each zone may be generated and optionally transmitted to a remote host.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
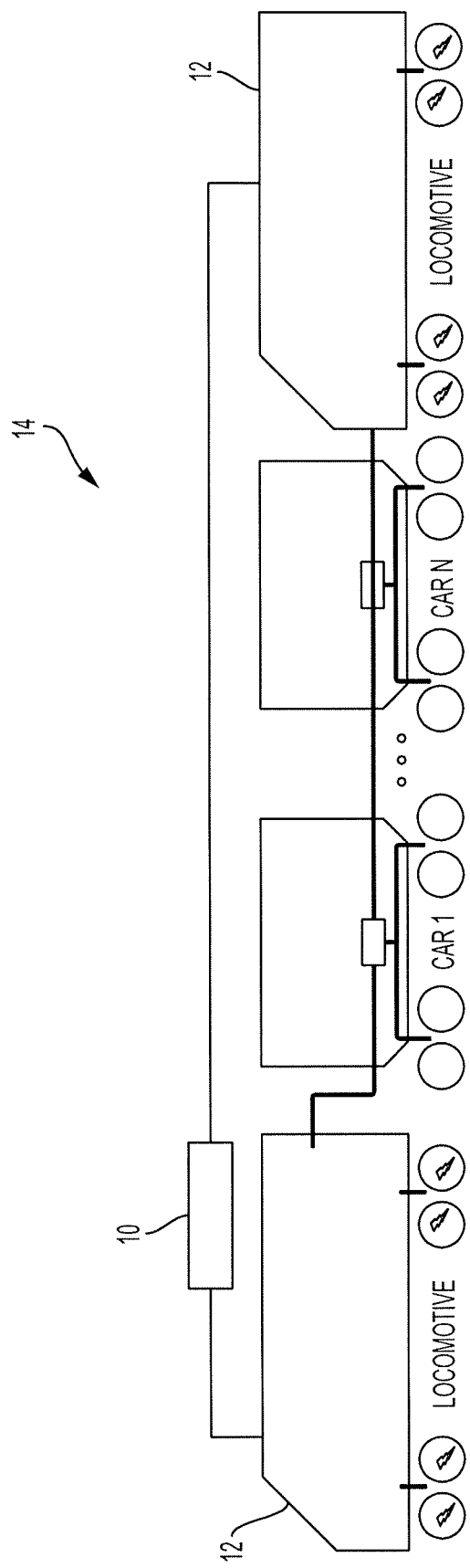
FIG. 1 is a schematic of a train having an emission compliance system according to the present invention.
Figure 2:
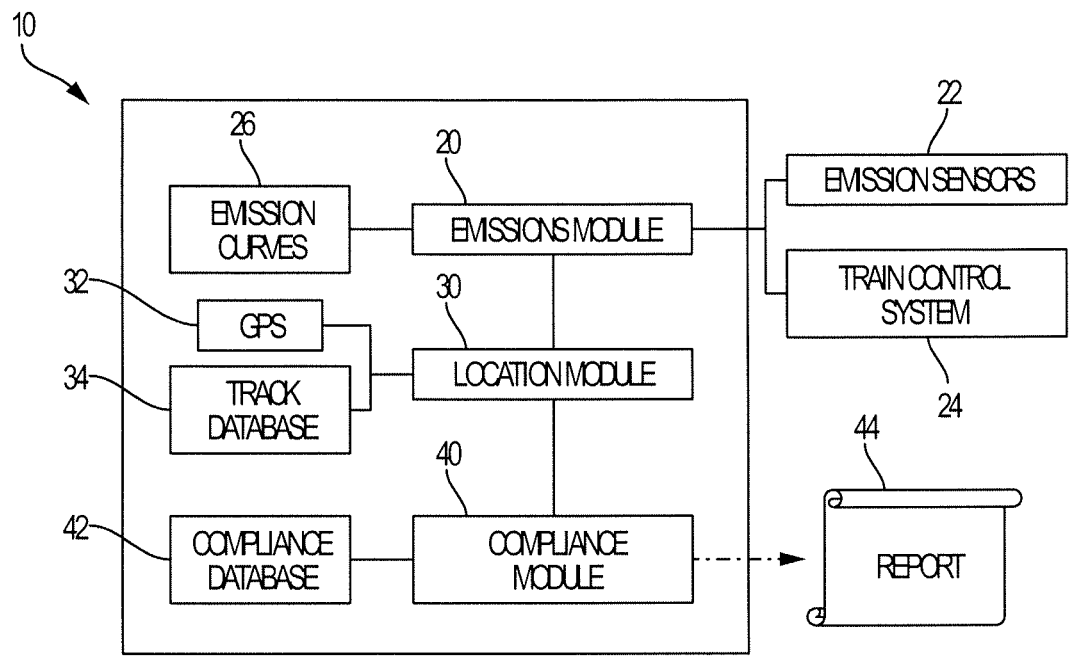
FIG. 2 is a schematic of an emission compliance system according to the present invention.
Figure 3:
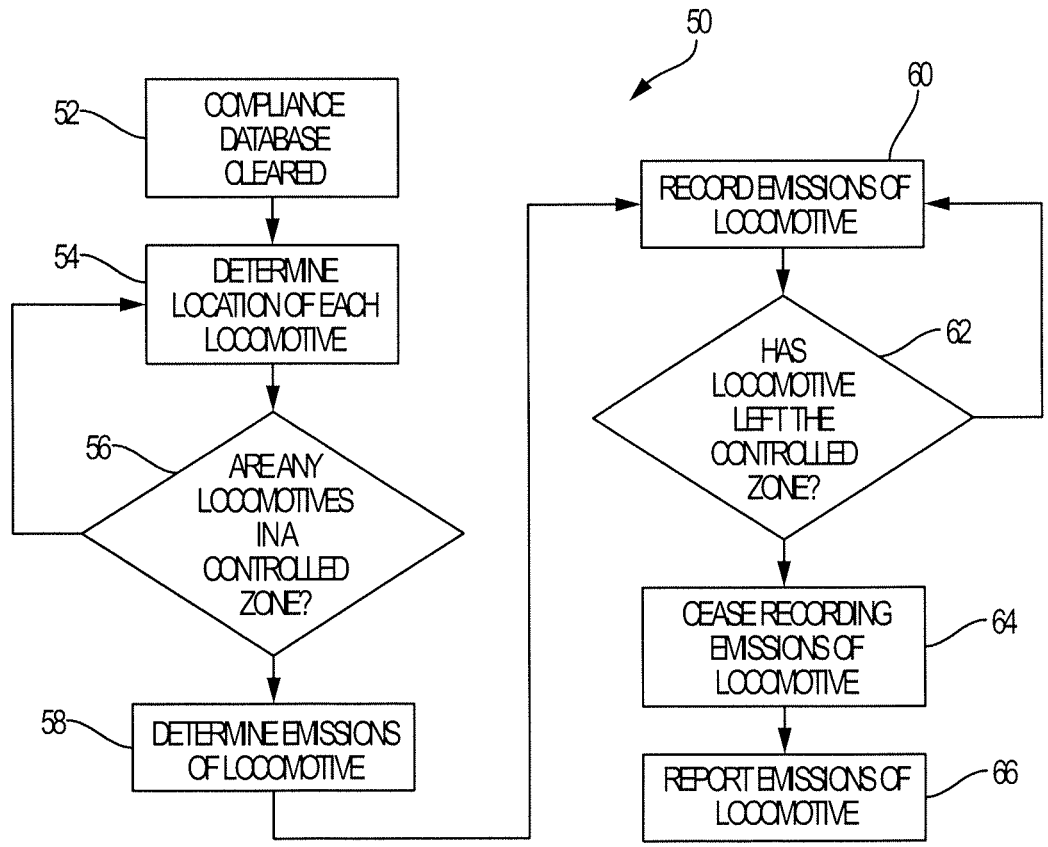
FIG. 3 is a flowchart of a method of performing emissions compliance using an emission compliance system according to the present invention.

Referring to the figures, wherein like numerals refer to like parts throughout, there is seen in FIG. 1, a system 10 for determining and recording the total emissions (e.g. carbon) from a group (not necessarily contiguous) of locomotives 12 in a train 14 which may additionally include one or more rail cars 16. System 10 is used to ensure that the emissions from the locomotives 12 are in compliance with any applicable emission policies where train 14 is being operated.

System 10 includes an emissions module 20 for determining current emissions. Module 20 can determine current emissions via sensors 22 positioned to take measurements of the emissions of interest from each locomotive 12 in train 14. Alternatively, emissions module 20 may be programmed to determine current emissions by interpolating the level of emissions from conventional train data. For example, emissions module 20 may use train data such as output power, force, engine speed, etc. acquired from a train control system 24 to extrapolate the current emissions. The relevant train data may be compared against a predetermined table that specifies the emissions of each locomotive based on manufacturing specifications, referred to as manufacturer curves. Instead of predetermined manufacturer emission curves, each locomotive 12 may be periodically subjected to a live emissions test that produces sufficient data to generate an emission curve that representing actual emissions from each locomotive as a function of running condition, locomotive velocity, temperature, etc. Thus, instead of using generic manufacturer curves for each locomotive based on its model number and manufactured specifications, the curves for each locomotive (identified by serial number or road number) may be used to more accurate determine emissions. The manufacturer or actual emission curves are stored in database of emission curves 26 that is accessible by emissions module 20. When locomotive running conditions are measured or gleaned from train control system 24, emissions activity may be determined or estimated by interpolating the running conditions into the emission curves 26. If actual emissions curves are absent for any reason, system 10 may use the manufacturer curves as a default.

Emission module 20 is provided with access to train specific data about the train on which system 10 is operating, such as the length of the train, the number and weight of the cars on the train, and the number and type of locomotives in the consist, as well as the location of each locomotives 12 within train 14 (car number) and a descriptor of each locomotive (model number and serial number/road number). Emission module 20 also has access to operational data, such as the commanded running state (e.g., throttle notch, dynamic brake notch, engine RPM, measured emissions, ambient temperature, ambient pressure, etc.) of each locomotive within the train, to determine the emissions of the train.

For example, all of the emissions calculations will have the form $$e_i = \int_0^T f(\vec{x})dt$$

Where $e_i$ represents the total emissions for locomotive i while it is present in an emissions-sensitive zone and T represents the time that locomotive i is in that zone.

$$E = \sum_{i=1}^n e_i$$

Where E is the total emissions for a given train and n represents the number of locomotives in the train.

The function $f$ represents the time rate of emissions for a locomotive. It can take several forms depending on the locomotive itself as well as the available data sources for calculating emissions rate. For example, in the case where the manufacturer provides detailed data about how the locomotive emits controlled pollutants, the function $f$ may be:

$$f=f(T,P,\rho,\omega,u,t)$$

Where T, P, and $\rho$ represent the thermodynamic state (temperature, pressure, density) of the air intake to the engine, $\omega$ represents the engine speed (e.g. RPM) and u represents the controlled inputs to the engine (e.g. state of the throttle valves).

The function $f$ may then consist of performing a multidimensional interpolation into manufacturer provided discrete tabular data using the measured values of all inputs at time t. It may also be some analytical function if such data is available.

In an additional usage of the form of $f$ above, the air conditions may not be directly known, but may be estimated a priori, for example via weather forecasts for the route of the train retrieved at the train's outset.

The form of $f$ above may be modified depending on the level of detail in the manufacturer provided data. Such data may, for example, not have a published dependency on condition of the intake air. Similarly, the function $f$ may have additional arguments that reflect other states of the engine's operation.

The form of $f$ above may also be modified via:

$$f=f(T,P,\rho,\omega,u,t)+C$$

In this case, the value of C will be established via acceptance testing at time of receipt/manufacture of the locomotive or via some periodic inspection of the locomotive.

In either case, the locomotive would be attached to some sensing apparatus (such as is commonly done in vehicle emissions testing in many U.S. states with a "tailpipe" sensor) and the level of emissions established. Knowing the running condition of the locomotive at the time this test is performed, the value of C is established for the locomotive by calibrating the emissions predicted by the manufacturer provided data/equations. If periodic inspections of the locomotive are performed in a similar fashion, then the value of C may be modified to reflect the outcome of these periodic inspections.

In a second case, an electronic nose (or equivalent sensor) is available to directly sense the rate of emissions from the locomotive's exhaust. In this case, $$f=r(t)$$

Where r(t) is the sensed rate of emissions from the sensor at time t.

System 10 also includes a location module 30 that is programmed to determine the geographical position of each locomotive as well as the geographical boundaries of emissions-controlled zones. For example, the State of California in the United States defines a zone having specific emission controls particular to that location). Present location information may be provided by a geographic positing system (GPS) 32 associated with system 10 (either dedicated or shared with the existing train control system) and emission-controlled zones may be made available and stored in a track database 34 accessible by location module 30.

System 10 further includes a compliance module 40 that is programmed to compile the total emissions of the train in each emission-controlled zone that train 14 traverses. Compliance module 40 is further programmed to store the relevant data in a compliance database 42 and to generate a report of the compiled total emissions for each zone. For example, compliance module 40 can display the result to the operator of the train or transmit a digital report 44 to a remote host. The report generated by compliance module 40 may thus be used to report actual emissions activity to the relevant agency responsible for ensuring compliance with each of the emissions-controlled zones that the train has traversed.

System 10 may implement an emission reporting method 50 that begins with the clearing on compliance database 52 at the outset of a trip. As train 14 is operated along a route, system 10 periodically determines the geographical location 54 of all locomotives within train 14 by receiving the geographical location of every locomotive from a GPS 32 associated with each locomotive or by extrapolating the location of each locomotive 12 from at least one GPS 32 and the train length/locomotive index information. Once the location of each locomotive is determined, system 10 checks 56 the location of each locomotive 12 with the location of any emission-controlled zones in emission curve database 34 to determine whether each locomotive 12 is in a zone. If any locomotive is in a zone at check 56, system 10 determines the emissions of that locomotive 58. This step of estimation may vary depending on the type of data that is available for each locomotive. In the most straightforward case, locomotive 12 is outfitted with one or more sensors 22 that directly sample the engine exhaust and transmit a signal representing the present rate of emissions to system 10. Alternatively, system 10 may sample the measured running condition of that locomotive (throttle notch, engine RPM, etc.) and estimate the present rate of emissions of controlled gases (NOx, $CO_2$, etc.) generated by that locomotive 12. Emissions may be estimated by using manufacturer-provided emission curves for every locomotive model number in the train and then interpolating from the curves using the measured running condition of the locomotive (engine RPM, throttle notch, etc.). If the emission curves require ambient pressure and temperature, system 10 may use air temperature/pressure data from sensors 22 mounted on the locomotive, or communicate with an internet (or other computer network) server that provides the relevant weather data. In the event that necessary data is not available, such as when actual pressure/temperature data for the geographical location of the locomotive is not known, system 10 can record all of the known data and then calculate emissions retroactively when the unknown data is available. Regardless of the particular approach, system 10 records the emissions 60 of each locomotive 12. At trip completion, another location check 62 is used to determine where any locomotives 12 have exited the emissions controlled zone, or reached some other pre-defined interval or location. If not, recording of emissions continues at step 60. If check 62 determines that locomotives 12 have left a designated zone, recording of emissions activity ceases 64. Process 50 may then conclude with reporting of total emissions of each locomotive 66, depending on the requirements of the operating railroad and the administrator of the emissions-controlled zone. For example, the total estimated emissions of locomotives while the train was located within the zone may be collected into report 4. Alternatively, or in addition thereto, a digital version of report 44 containing the relevant data may be transmitted to a remote host, such as the railroad and/or the emission zone administrator.

Referring to FIG. 4, system 10 may include an emission control module 70 coupled to emissions module 20 and/or location module 30. Emission control module 70 is programmed to provide instructions or commands to train control system 24 to control the state of locomotives 12 to provide a desired output characteristic while minimizing emissions. Emission control module 70 may thus set the throttle/brake position of each locomotive 12 based on the amount of tractive effort desired from the locomotive consist in manner that achieves the desired tractive effort while minimizing emissions from each locomotive, the entire consist, or both. Emission control module 70 can determine the emissions of each locomotive 12 using emissions module 20 as described above (or be separately programmed to perform the same operations). Emission control module 70 is also programmed to perform an optimization to determine the independent throttle/brake position of each locomotive 12 that provides the desired output while minimizing the total emissions (e.g. carbon) from the locomotive consist. The optimization can be a straightforward brute force search as the number of state variables is small (throttle notch per locomotive) and the values of each state variable are discrete (again, throttle notch). In the event that train control system 24 is able to assign a continuous, specific value of the input to each locomotive (tractive effort, engine RPM, etc.), then a brute force search may no longer be appropriate and any of the various algorithms known in the art may be used to achieve a constrained optimization. For example, approaches such as interior point methods, active point methods, etc. may be used for the optimization.

It should be recognized that emission control module 70 may be provided in conjunction with location module 30 as described herein so that emissions are controlled in a particular manner based on geographic location and the presence of any controlled emission zones. As a result, emission control module 70 may be programmed to attenuate emissions by controlling locomotives 12 in a particular manner based on whether locomotives are in an environmental zone restricting the amount of emissions.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A system for tracking train emissions, comprising:
   a locomotive having a train control system installed in the locomotive and sensors interconnected to the train control system for collecting data representing a plurality of actual running conditions of the locomotive and a plurality of ambient weather conditions;
   a track database installed in the locomotive and associated with the train control system and containing a plurality of emission-controlled zones through which the locomotive will travel over a predetermined route stored therein;
   a database installed in the locomotive and having an emission curve representing the amount of emissions generate by the locomotive under predetermined running conditions, wherein the emission curve is based on actual emissions recorded from the locomotive as a function of running conditions, locomotive velocity, and temperature during a live emissions test;
   an emissions module installed in the locomotive and associated with the train control system and the database, wherein the emissions module is programmed to determine the amount of emissions emitted by the locomotive of the train over time using the actual running conditions of the locomotive-and the ambient weather conditions as determined by the train control system and the emission curve of the database;
   a location module associated with the train control system and having access to plurality of emission-controlled zones stored in the track database that is programmed to track the location of the locomotive over the predetermined route as it traverses each of the plurality of emission-controlled zones; and
   a compliance module programmed to receive the amount of emissions emitted by the locomotive of the train over time and to record the amount of emissions emitted by the locomotive over time in each of the plurality of emission-controlled zones.

2. The system of claim 1, further comprising a locomotive consist including the locomotive and at least one other locomotive, wherein the emissions module is programmed to determine the amount of emissions of all locomotives and the compliance module is programmed to record the amount of emissions emitted by all of the locomotives.

3. The system of claim 2, wherein the compliance module is further programmed to record the amount emissions emitted by all of the locomotives in the train in the predetermined geographic location as determined by the location module.

4. A method of tracking train emissions, comprising the steps of:
- determining a plurality of actual running conditions of the locomotive and a plurality of ambient weather conditions using a train control system installed in the locomotive and having sensors interconnected to the train control system for collecting data representing the plurality of actual running conditions of the locomotive and the plurality of ambient weather conditions;
- providing a database in the locomotive that has an emission curve representing the amount of emissions generate by the locomotive under predetermined running conditions;
- providing a track database in the locomotive that is associated with the train control system and that contains a plurality of emission-controlled zones through which the locomotive will travel over a predetermined route stored therein;
- determining the amount of emissions emitted by a train over time with an emissions module associated with the train control system and the database, wherein the emissions module is programmed to determine the amount of emissions emitted by a locomotive of a train over time using the actual running conditions of the locomotive, and the ambient weather conditions as determined by the train control system and the emission curve;
- tracking the location of the train using a location module associated with the train control system, having access to plurality of emission-controlled zones stored in the track database, and programmed to track the location of the locomotive over the predetermined route as it traverses each of the plurality of emission-controlled zones; and
- recording the amount of emissions emitted by the train in each of the plurality of emission-controlled zones.

5. The method of claim 4, further comprising the step of compiling a total amount of emissions of the train by tracking the amount of emissions emitted by a train over time for the entire time the train is in the at least one geographic location having emission regulations.

6. The method of claim 5, further comprising the step of generating a report of the compiled total emissions for each zone.

7. The method of claim 6, further comprising the step of transmitting the report to a remote host.

* * * * *